United States Patent
Diehl et al.

(10) Patent No.: US 6,660,144 B2
(45) Date of Patent: Dec. 9, 2003

(54) ELECTROCHEMICAL SENSOR

(75) Inventors: Lothar Diehl, Stuttgart (DE); Harald Neumann, Oberriexingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/958,371

(22) PCT Filed: Jan. 27, 2001

(86) PCT No.: PCT/DE01/00332

§ 371 (c)(1),
(2), (4) Date: Mar. 25, 2002

(87) PCT Pub. No.: WO01/57511

PCT Pub. Date: Aug. 9, 2001

(65) Prior Publication Data

US 2002/0112958 A1 Aug. 22, 2002

(30) Foreign Application Priority Data

Feb. 4, 2000 (DE) .......................................... 100 04 959

(51) Int. Cl.$^7$ ............................................. G01N 27/407
(52) U.S. Cl. ...................................... 204/426; 204/427
(58) Field of Search ................................. 204/421–429

(56) References Cited

U.S. PATENT DOCUMENTS

| | | | | |
|---|---|---|---|---|
| 4,655,901 A | * | 4/1987 | Mase et al. |
| 5,098,549 A | | 3/1992 | Friese et al. |
| 5,395,506 A | | 3/1995 | Duce et al. |
| 5,419,828 A | | 5/1995 | Nakano et al. |
| 5,529,677 A | * | 6/1996 | Schneider et al. |

* cited by examiner

Primary Examiner—T. Tung
(74) Attorney, Agent, or Firm—Kenyon & Kenyon

(57) ABSTRACT

An electrochemical sensor has a sensor element, and is used to determine a gas concentration of a gas to be analyzed. The sensor element has a first solid electrolyte layer, an electrode that includes an electrode surface and an electrode lead, and a second solid electrolyte layer; a gas channel being introduced into the first solid electrolyte layer in such a manner, that the electrode is situated in a first, clamped region between the first and the second solid electrolyte layers, and in a second, open region between the second solid electrolyte layer and the gas compartment. In a transition region between the clamped region and the open region, the electrode borders on a layer pattern, which is constructed in such a manner, that the electrode is subjected to a lower pressure during a laminating procedure.

10 Claims, 3 Drawing Sheets

ELECTROCHEMICAL SENSOR

BACKGROUND INFORMATION

Electrochemical sensors are known, for example, from the Automotive Electronics Handbook (1994), chapter 6, Wiedenmann et al., "Exhaust Gas Sensors", for use in analyzing exhaust gas of internal combustion engines. Such sensors include a planar sensor element, which is manufactured by the printing ceramic foils onto it, which have electrodes, by laminating the planar sensor element together using a compression force applied by means of a compression pad, and by sintering it. In the case of these sensor elements, there is, however, the danger of the electrode adjacent to the one gas channel being partially or completely severed during lamination, by the use of the compression force, so that normal use is impaired or excluded.

SUMMARY OF THE INVENTION

In comparison with the related art, the electrochemical sensor of the present invention has the advantage of ensuring to the greatest possible extent, that the electrode or the electrode leads are routed continuously, without being pinched or broken, even in a transition region between the gas channel and adjacent solid electrolyte foils.

By selecting a suitable layer pattern in the transition region of the electrode, the electrode present in the laminating process in the form of a paste is subjected to a lower pressure, so that the pinching of the electrode in the clamped (squeezed) region and the transport of the electrode into the open region are prevented to the greatest possible extent. Therefore, a reduction in the cross-sectional area of the electrode in the transition region, or even a complete separation of the electrode, is prevented, which means that a lower production variance is achieved, e.g. with regard to the electrical resistance of the electrode, and less manufacturing waste is generated.

The method of the present invention for manufacturing an electrochemical sensor ensures that a lower local pressure is applied to the electrode while laminating it together, and therefore, that the electrode is produced in a manner allowing it to be unpinched and unbroken to the greatest possible extent.

DETAILED DESCRIPTION

Figure 1:
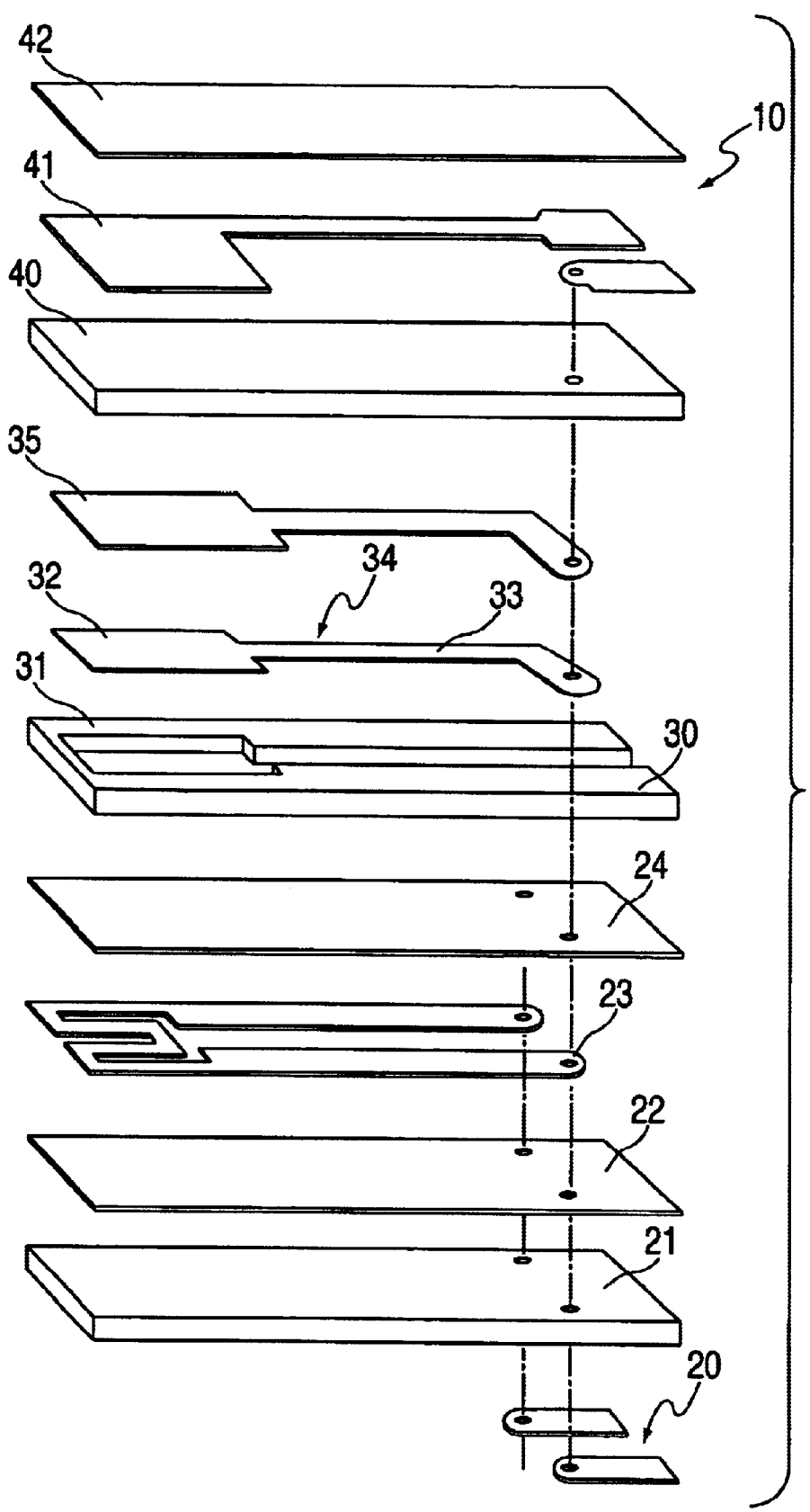
FIG. 1 shows an exploded view of a specific embodiment of a sensor element according to the related art.

FIG. 1 shows a planar sensor element 10 of an electrochemical sensor for analyzing gases, which is known per se from the related art. Sensor element 10 has electrical connection contacts 20, a first solid electrolyte foil 30 in which a gas channel 31 is formed that is connected, on the terminal end, via an opening, to a gas compartment situated outside sensor element 10, an electrode 34 as a reference electrode which includes an electrode surface 32 and an electrode lead 33, a foil binding layer 35, a second solid electrolyte foil 40, a measuring electrode 41, and a covering layer 42, as well as a further solid electrolyte foil 21 as a heater foil, a first insulating layer 22, a heater 23, and a further insulating layer 24. Solid electrolyte foils 21, 30, 40 can also be manufactured as solid electrolyte layers.

Figure 2:
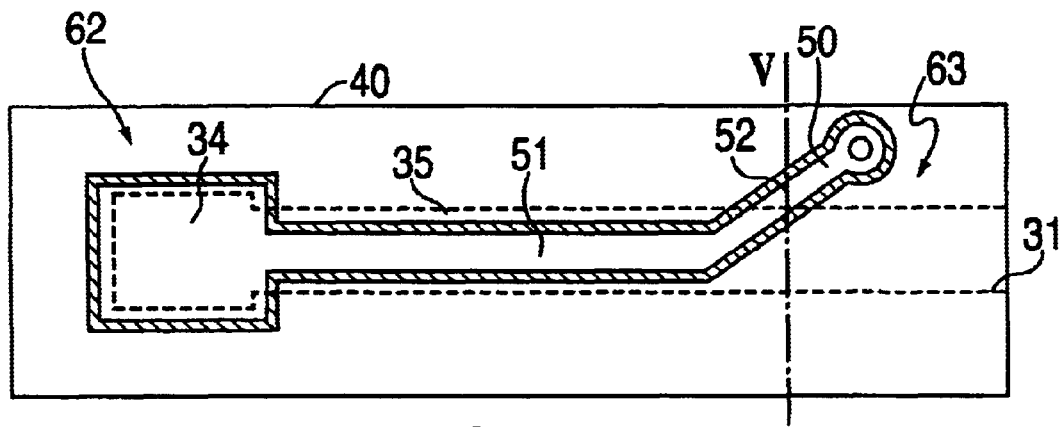
FIG. 2 shows a plan view of a solid electrolyte foil of the sensor element according to the related art.

FIG. 2 shows the known sensor element according to FIG. 1, as a plan view of the large surface of second solid electrolyte foil 40, along with foil-bonding layer 35 and electrode 34. Electrode 34 is situated in a first, clipped region 50, between first solid electrolyte foil 30 and second solid electrolyte foil 40, and in a second, open region 51, between gas channel 31 and second solid electrolyte foil 40. The position of gas channel 31 is indicated by dotted lines.

Figure 3:
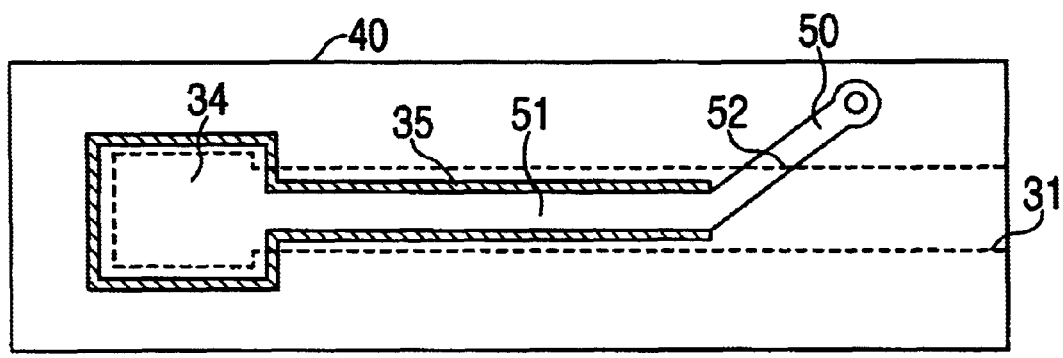
FIG. 3 shows a plan view of a solid electrolyte foil of the present invention's sensor element, according to a first specific embodiment.

FIG. 3 shows a first exemplary embodiment of the present invention, in which, in a revision of the known design according to FIG. 2, foil-bonding layer 35 is left out (cut out) in transition region 52, between clamped region 50 and open region 51 of electrode 34. Other designs are conceivable, in which electrode 34 is surrounded by at least one further foil-bonding layer that is also left out in transition region 52. In the case of a plurality of foil-bonding layers, the recesses (cut outs) can be set up step-by-step. By leaving out at least one foil-bonding layer 35, the height of the material between first and second solid electrolyte layers 30, 40 is reduced in transition region 52, which means that, during lamination, a lower pressure is applied to electrode 34 in transition region 52.

Figure 4:
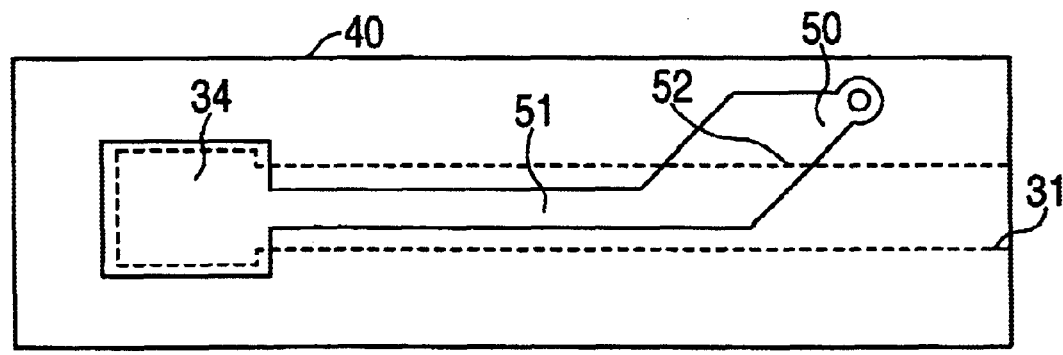
FIG. 4 shows a plan view of the solid electrolyte foil, in accordance with a further embodiment of the sensor element of the present invention.

FIG. 4 shows a plan view of a further exemplary embodiment according to the present invention, where, in a modification of the known design according to FIG. 2, electrode 34 is considerably wider along the boundary between first region 50 and second region 51, than in the region of gas channel 31. This reduces the danger of electrode 34 separating in transition region 52.

Figure 5A:
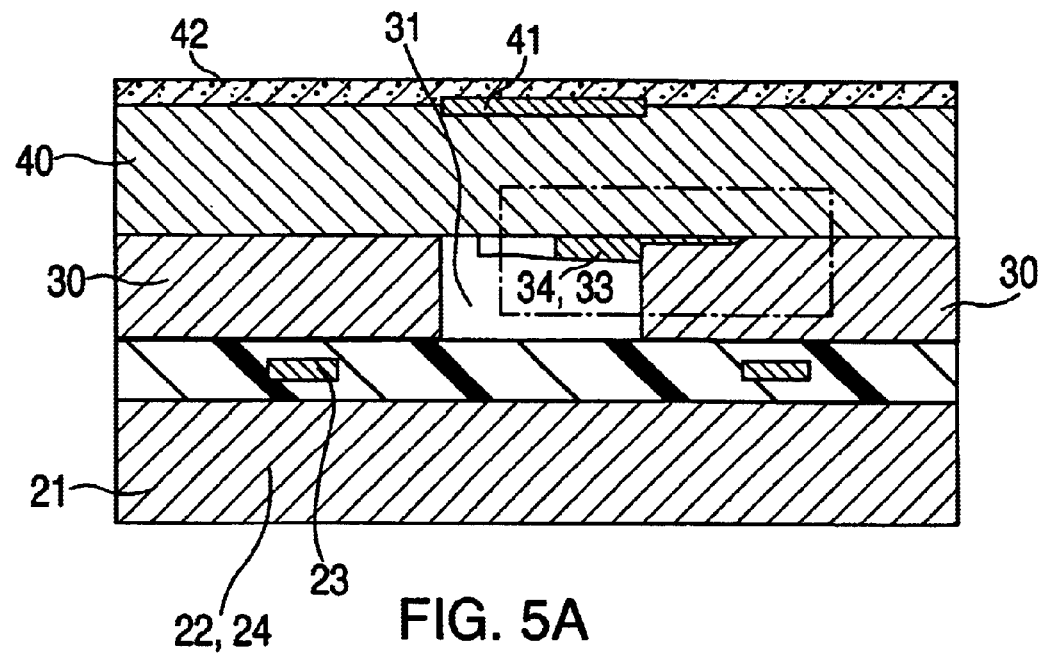
FIG. 5a shows a sectional view of the sensor element according to the related art, along line V—V in FIG. 2.

FIG. 5a shows a sectional view of the transition region 52 of electrode 34, for a sensor element according to FIG. 1, which is known per se. It is clear from the sectional view, that electrode lead 33 is pinched at the edge of gas channel 31, between solid electrolyte foils 30 and 40; in response to a high compression force, the edge being able to cut through electrode lead 33 at this position.

Figure 5B:
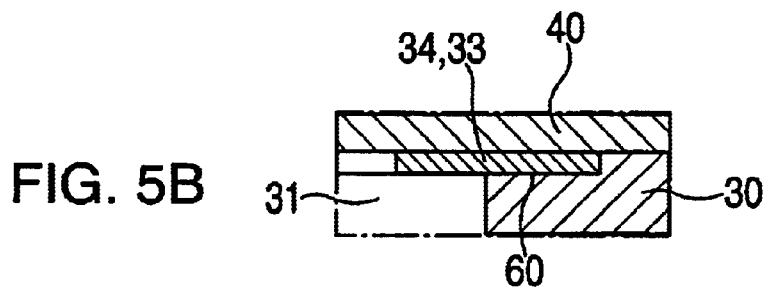
FIG. 5b shows a detail B of FIG. 5a, in accordance with an embodiment of the present invention.
Figure 5C:
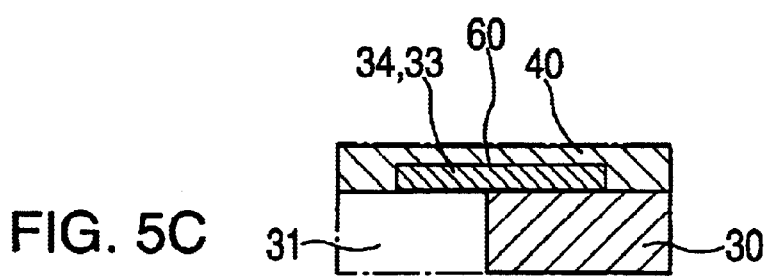
FIG. 5c shows a detail B of FIG. 5a, in accordance with another embodiment of the present invention.
Figure 5D:
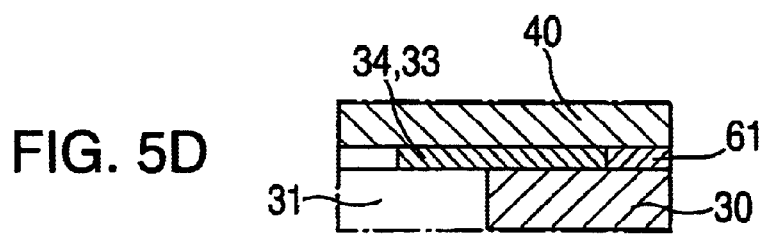
FIG. 5d shows a detail B of FIG. 5a, in accordance with yet another embodiment of the present invention.

FIGS. 5b through 5d show specific embodiments of transition region 52 according to the present invention. In FIGS. 5b and 5c, a recess 60 accommodating electrode lead 33 is imprinted into first solid electrolyte layer 30 and second electrolyte layer 40, respectively. Represented in FIG. 5d is a specific embodiment, which has a compensating layer 61 next to electrode lead 33. The layer patterns of the specific embodiments of transition region 52 shown in FIGS. 5b through 5d prevent electrode lead 33 from being pinched during the laminating procedure.

In further embodiments of the present invention, which are not shown, recess 60 or compensating layer 61 can be finished in steps, in which, during lamination, a more uniform pressure distribution on electrode 34 is achieved in transition region 52.

In another specific embodiment, which is not represented in further detail, transition region 52 is placed in a region of the sensor element, in which gas channel 31 is particularly narrow, e.g., in the case of the sensor element 10 shown in FIG. 2, not in measuring-end region 62 having a wide gas channel 31, but rather in terminal-end region 63 having a narrow gas channel 31. This reduces the local pressure in the transition region, during lamination.

In a development of the present invention regarding the method for manufacturing the sensor element of the present invention, a hard compression pad is used during lamination, so that a pressure increase in the area of gas channel 31, and thus, in transition region 52, is prevented during lamination.

What is claimed is:

1. An electrochemical sensor for determining at least one of gas components and gas concentrations in gas mixtures, the sensor comprising a sensor element, the sensor element including:

a first solid electrolyte layer containing a gas channel;

a second solid electrolyte layer; and an electrode including an electrode surface and an electrode lead, the electrode being situated in a first, clamped region between the first and second solid electrolyte layers and in a second, open region between the second solid electrolyte layer and the gas channel, at least one of the first solid electrolyte layer and the second electrolyte layer including a recess in a transition region between the clamped region and the open region, the recess accommodating the electrode such that the electrode is subjected to a lower pressure during a laminating procedure.

2. The sensor according to claim 1, wherein the recess is a stamped recess for the electrode.

3. The sensor according to claim 1, wherein the transition region is situated in a region of the sensor element in which a surface area of the gas channel is low.

4. The sensor according to claim 1, wherein the electrode is substantially wider along a boundary between the first and second regions than in a region of the gas channel.

5. A electrochemical sensor for determining at least one of gas components and gas concentrations in gas mixture, the sensor comprising a sensor element, the second element comprising:

a first solid electrolyte layer containing a gas channel;

a second solid electrolyte layer;

an electrode including an electrode surface and an electrode lead, the electrode being situated in a first, clamped region between the first and second solid electrolyte layers and in a second, open region between the second solid electrolyte layer and the gas channel; and at least one foil-bonding layer situated between the electrode and one of the first and second solid electrolyte layers, and wherein, in a transition region between the first region and the second region, at least one of the at least one foil-bonding layer is left out.

6. An electrochemical sensor for determining at least one of gas components and gas concentrations in gas mixtures, the sensor comprising a sensor element, the sensor element including:

a first solid electrolyte layer containing a gas channel;

a second solid electrolyte layer;

an electrode including an electrode surface and an electrode lead, the electrode being situated in a first, clamped region between the first and second solid electrolyte layers and in a second, open region between the second solid electrolyte layer and the gas channel; and a compensating layer situated next to the electrode in a transition region between the first region and the second region, the compensating layer configured to compensate for a thickness of the electrode.

7. The sensor according to claim 6, wherein the compensating layer is a same thickness as the thickness of the electrode.

8. An electrochemical sensor for determining at least one of gas components and gas concentrations in gas mixtures, the sensor comprising a sensor element, the sensor element including:

a first solid electrolyte layer containing a gas channel;

a second solid electrolyte layer; and an electrode including an electrode surface and an electrode lead, the electrode being situated in a first, clamped region between the first and second solid electrolyte layers and in a second, open region between the second solid electrolyte layer and the gas channel, at least one of the first solid electrolyte layer and the second electrolyte layer including a recess in a transition area between the clamped region and the open region, the recess accommodating the electrode.

9. An electrochemical sensor for determining at least one of gas components and gas concentrations in gas mixtures, the sensor comprising a sensor element, the sensor element including:

a first solid electrolyte layer containing a gas channel;

a second solid electrolyte layer; and an electrode including an electrode surface and an electrode lead, the electrode being situated in a first, clamped region between the first and second solid electrolyte layers and in a second, open region between the second solid electrolyte layer and the gas channel, one of the first solid electrolyte layer and the second electrolyte layer including a recess in a transition area between the clamped region and the open region, the recess accommodating the electrode.

10. A electrochemical sensor for determining at least one of gas components and gas concentrations in gas mixtures, the sensor comprising a sensor element, the second element comprising:

a first solid electrolyte layer containing a gas channel;

a second solid electrolyte layer;

an electrode including an electrode surface and an electrode lead, the electrode being situated in a first, clamped region between the first and second solid electrolyte layers and in a second, open region between the second solid electrolyte layer and the gas channel; and at least one foil-bonding layer situated between the electrode and the first solid electrolyte layer, and wherein, in a transition region between the first region and the second region, at least one of the at least one foil-bonding layer is left out.

\* \* \* \* \*